United States Patent [19]
Petree et al.

[11] 3,981,712
[45] Sept. 21, 1976

[54] TREATMENT OF IRON DEFICIENCIES IN PLANTS WITH IRON COMPLEXES OF ETHYLENE-BIS-($\alpha$-IMINO-2-HYDROXYARYL ACETIC ACIDS)

[75] Inventors: Harris E. Petree, Spanish Fort; Joseph W. Stutts, Jackson, both of Ala.

[73] Assignee: Ciba-Geigy Corporation, Ardsley, N.Y.

[22] Filed: July 3, 1975

[21] Appl. No.: 593,099

Related U.S. Application Data

[62] Division of Ser. No. 391,401, Aug. 24, 1973, Pat. No. 3,903,119.

[52] U.S. Cl. ............................ 71/1; 71/DIG. 2; 260/429 J; 260/439 R
[51] Int. Cl.² ........................................ C07F 15/02
[58] Field of Search ............................ 71/1, DIG. 2; 260/439 R, 429 J

[56] References Cited
UNITED STATES PATENTS

| | | | |
|---|---|---|---|
| 2,824,128 | 2/1958 | Dexter | 260/439 R |
| 3,028,407 | 4/1962 | Knell et al. | 71/DIG. 2 X |
| 3,711,525 | 1/1973 | Hennart | 260/439 R |

*Primary Examiner*—Frank A. Spear, Jr.
*Assistant Examiner*—Ferris H. Lander
*Attorney, Agent, or Firm*—Karl F. Jorda

[57] ABSTRACT

Compositions and methods useful for the treatment of iron deficiencies in plant utilizing new iron complexes of ethylene-bis($\alpha$-imino-2-hydroxyaryl-acetic acids) containing sulfonic acid groups are disclosed in which the molar ratio of iron to ligand is from about 1.1:1 to 3:1. These complexes are stable at pH values of from about 6.0 to 9.0.

4 Claims, No Drawings

TREATMENT OF IRON DEFICIENCIES IN PLANTS WITH IRON COMPLEXES OF ETHYLENE-BIS-(α-IMINO-2-HYDROXYARYL ACETIC ACIDS)

CROSS-REFERENCE TO RELATED APPLICATION

This is a division of application, Ser. No. 391,401, filed Aug. 24, 1973, now U.S. Pat. No. 3,903,119, issued Sept. 2, 1975.

The present invention relates to iron complexes of ethylene-bis-(α-imino-2-hydroxyaryl acetic acids) containing one or more sulfonic acid groups at each of the aryl radicals in which the molar ratio of iron to ligand is from 1.1:1 to 3:1. This invention further pertains to compositions containing said iron complexes as active substances and to methods of treatment of iron deficiencies in plants with said iron complexes.

It is known that iron chelates of N,N'-bis(o-hydroxybenzyl)-ethylenediaminediacetic acids and ethylene-bis-(α-imino-2-hydroxyphenylacetic acids), the phenyl radicals of which may be substituted by halogen atoms or alkyl, alkoxy, sulfonic acid or carboxylic acid groups, and derivatives thereof, are useful for the treatment of iron deficiencies in plants and/or mammals. In these known chelates the organic molecule was combined with ferric or ferrous iron in a molar ratio of 1:1. (See, e.g., U.S. Pat. Nos. 2,921,847, 3,005,848, 3,038,793 and 3,367,834.)

The present invention provides new iron complexes which are more effective, and therefore more economical, in supplying micro-nutrients to plants. More particularly, complexes of a ligand and iron are provided, wherein the molar ratio of ligand to iron is from about 1:1.1 to 1:3, and wherein the ligand has the following formula

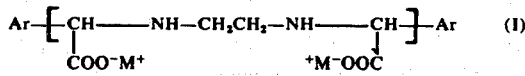

In this formula M is hydrogen or an alkali metal ion and Ar represents an ortho-hydroxy-aryl derivative of a mono- or poly-nuclear aromatic group substituted with one or more sulfonic acid groups, such as mononuclear aromatic compounds of the formula:

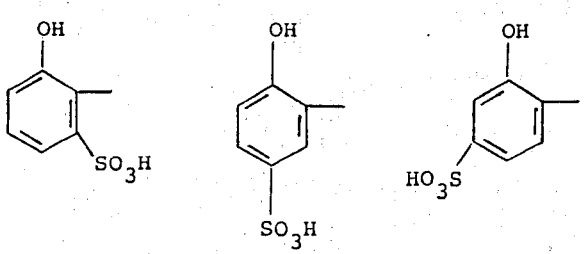

monosulfonated 2-naphthol derivatives of the formula:

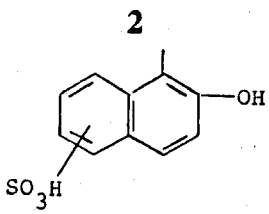

wherein —SO$_3$H is in the 3,4,5,6,7 or 8 positions, and di- and tri-sulfonic acid derivatives of 2-naphthol, with —SO$_3$H groups being in the 3,4,5,6,7 or 8 positions.

Additionally, Ar represents α-hydroxy-substituted anthracene or phenanthrene sulfonic acids of the formula

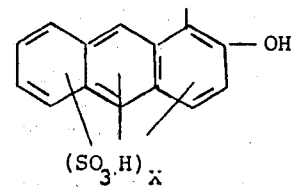

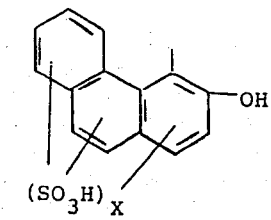

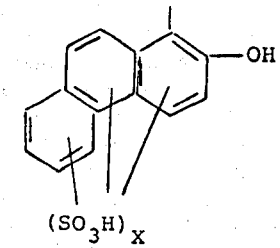

wherein X is 1 to 3.

Furthermore, available substituent points in the aromatic nucleus may be substituted, for enhancement of biological properties, by such groups as halogen atoms, lower alkyl, lower alkoxy, lower alkylthio, lower alkylsulfoxy, lower alkylsulfone, nitro, amino, lower alkylamino, lower dialkylamino and acylamido. Heterocyclic groups containing N, S, O, P, and other atoms are further possible substituents.

More particularly, complexes of ligands of an ethylene-bis-(α-imino-2-hydroxyarylacetic acid) having the general formula

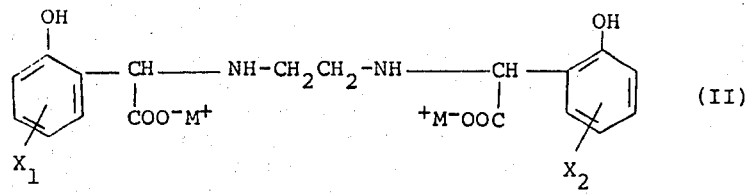

and iron are provided, wherein the molar ratio of ligand to iron is from 1.0:1.1 to 1:0:3.0, and $X_1$ and $X_2$ are each linked in the 3-, 4- or 5-position to each benzene nucleus and each represents $-SO_3^-M^+$, wherein M is hydrogen or an alkali metal ion.

If M represents an alkali metal ion, this may be lithium or potassium and, more especially, the sodium ion.

The substituents $X_1$ and $X_2$ are each preferably linked in the 5-position to the respective benzene nucleus, and each represents $-SO_3^-M^+$, M being hydrogen or the sodium ion.

Iron complexes as defined are preferred wherein the molar ratio of ligand to iron is from about 1:1.5 or 1:1.8 to 1:2.0.

That ligands of formula I combine with iron in a molar ratio of from about 1:1.1 to 2.0 or >2 is surprising both in view of the teachings of the prior art and the finding that similar ligands, such as, N,N'-bis-(2-hydroxy-5-sulfobenzyl)-ethylenediaminediacetic acids, are unable to chelate iron at molar ratios greater than one.

As regards the nature of the complexes of this invention, one iron is chelated by one of the ligands of formula I in the usual manner to form a 6-coordinate octahedral complex, but it is not known how additional second atoms of iron are bound to the ligand.

The ligands of Formula I are known per se (see e.g., U.S. Pat. No. 3,005,848) and can be prepared by conventional methods, as for instance by reacting a hydroxyphenylsulfonic acid, or an alkali metal salt thereof, with glyoxylic acid or an alkali metal salt thereof, especially sodium glyoxylate, and ethylenediamine, in a molar proportion of at least 2:2:1. The reaction is advantageously conducted in an aqueous or aqueous-organic medium, at a temperature between about 70° and 100°C, preferably about 80° and 90°C, and at a pH between 8 and 10. Suitable organic solvents are water-miscible solvents, such as methyl ethyl and isopropyl alcohol. It is also possible to use sodium dichloroacetate in place of the glyoxylic acid or its alkali metal salt, in the above synthesis. In this case, it is necessary, however, to add two moles of base for each mole of sodium dichloroacetate used in order to maintain the desired degree of alkalinity during the reaction.

Isolation of the ligand of Formula I from the resultant brown solution is not necessary, though possible, for instance by extraction of the dried reaction mixture with a suitable solvent such as methyl, ethyl or isopropyl alcohol, acetone, chlorinated hydrocarbons or dimethylformamide, at a pH value of the reaction mixture of about 1.0.

According to a preferred embodiment the solution of the desired ligand is treated directly, in a manner known per se, with a suitable water-soluble ferric salt, such as ferric chloride, sulfate, nitrate or acetate. Before the addition of the ferric salt, the pH of the reaction mixture is advantageously adjusted to about 10.0 to 11.0, e.g. by means of aqueous sodium hydroxide solution, and the solution is cooled to about 30° to 50°C. This temperature is maintained throughout the addition of the ferric salt, the latter being preferably employed in the form of an aqueous solution. The iron content of said aqueous solution of the ferric salt should be preferably somewhat in excess over the desired ligand/Fe molar ratio in the complex to be produced, e.g., an about 10–30% excess over the ligand/Fe molar ratio of from about 1:1.1 to 1:3 should be employed. After all the ferric salt has been added, the pH value of the reaction mixture is again adjusted to about 6.5 to 8.0, preferably by the addition of aqueous sodium hydroxide solution. A red-purple solution is obtained. The complex can be isolated by known methods such as evaporating the reaction mixture to dryness.

Additionally, ferrous ($Fe^{++}$) salts may be used as sources of iron. In general, these will be transformed to ferric or ferroso-ferric complexes due to the tendency of these to approach the $Fe^{+++}$ oxidation state by abstraction of oxygen from air, ligand, or reaction mixture.

It is also possible to use sodium dichloroacetate in place of the glyoxylic acid or its alkali metal salt, in the above synthesis. In this case, it is necessary, however, to add two moles of base for each mole of sodium dichloroacetate used in order to maintain the desired degree of alkalinity during the reaction.

In contrast to prior art compositions the complexes of this invention meet also present day ecological needs. These complexes may be prepared in simple chemical reactors (stirred vessel equipped for heating or cooling). The chelation may be accomplished in the same vessel, and, since the entire mixture is a soluble, stable solution, it can be isolated by drying (or used as is). In either case no effluent is generated by this process, and no biological, chemical or total oxygen demand byproducts are present which require effluent treatment. Furthermore, due to the higher iron to ligand ratio the amount of iron complex for treatment of iron deficiencies may be reduced. The product, when dried, is a crystalline solid which is dense (55 lbs./cu. ft.), rapidly and readily redissolves in water for its application as an agricultural nutrient, and is free flowing and relatively non-dusting, an advantage over earlier discovered materials such as CHEL 138 NaFe (EDDHA NaFe, or, ethylenediaminedi-2-hydroxyphenyl-acetic acid, NaFe salt).

The following examples serve to illustrate the preparation of the novel iron complexes of the present invention but are not to be considered limiting.

EXAMPLE 1

Ferric Complex of Ethylene-bis-($\alpha$-imino-2-hydroxy-5-sulfophenylacetic Acid).

To a reaction flask were added 100 g of water, 528 g. (2.0 mol) of a 66% aqueous solution of p-phenolsulfonic acid, and 296 g. (2.0 mol) of 50% glyoxylic acid. Then 335 g. (4.2 mol) of a 50% aqueous sodium hydroxide solution were slowly added at 30°C until a pH of 6.0 was reached. Finally, 66 g. (1.0 mol) of 92% ethylenediamine were charged at the same temperature, and the pH of the reaction mixture was adjusted to 9.0 by the addition of further aqueous sodium hydroxide solution. The reaction mixture was heated to 85°C for 4 hours. After completion of the reaction mixture was cooled to 40°C, and the pH thereof was raised to 10.8 to 11.0 by the addition of 50% aqueous sodium hydroxide solution. An assay of the solution by copper chelometric titration analysis showed a yield of product ethylene-bis-($\alpha$-imino-2-hydroxy-5-sulfophenylacetic acid) of 70.0%. 784 g. ferric sulfate solution as 10% Fe (1.4 g.-atoms) were then slowly added at 40°–50°C, followed by the addition of 50% aqueous sodium hydroxide solution to adjust the pH to 6.5. The solution became deep red, and was then evaporated to dryness. The yield of the solid was 1045 g; % Fe = 7.5; molar ratio ligand: Fe = 1:2.

EXAMPLE 2

Ferric Complex of 1,1'-ethylene-bis-($\alpha$-imino-2-hydroxy-3,6-disulfo-2-naphthaleneacetic) Acid Similarly to the above, to a 3 l. reaction flask were charged 1300 g. of water, 696 g. (0.81 mol) of 2-naphthol-3,6-disulfonic acid, $Na_2$salt, ("R Salt") and 296 g. (2 mol) of 50% glyoxylic acid. The mixture was cooled to 0°–10°C and 66 g. (1 g-mol) of 91.5% ethylenediamine in water was added, allowing the mixture to reach 25°C and a pH of 3.5. The mixture was then heated at 45°C for 4 hours; a final pH of 3.1 was noted. Copper chelometric titration analysis indicated an 82% yield of 1,1'-ethylene-bis-($\alpha$-imino-2-hydroxynaphthalene-3,6-disulfo-acetic) acid. Chelation with iron was carried out in two steps. First, a 1:1 Fe-ligand chelate was synthesized by charging 291.4 g $FeCl_3$ solution (45%) based on copper chelometric assay of the ligand solution. Adjustment to pH 7 was carried out by addition of 456 g of 25% NaOH. Assay of the chelate solution spectrophotometrically showed a 1.37% soluble Fe content and the insolubles were measured at only 0.01%. After allowing for analytical sample removal, a second mole-equivalent of Fe was added by charging 266.4 g. $FeCl_3$ solution. After pH adjustment to 7 again the product solution was dried on a pilot plant drum dryer resulting in chelate containing 7.0% soluble Fe.

The iron complexes of the present invention are stable over a wide pH range, i.e. pH values ranging from about 6.0 to 9.0 and are thus suitable for the treatment of iron deficiencies occurring in plants grown on alkaline as well as neutral and slightly acid soils. The present invention thus also provides a composition for the treatment of iron deficiencies in plants which comprises, preferably, from about one-hundredth to about 50 percent by weight, of at least one complex of a ligand of Formula I and iron as hereinbefore defined as active ingredient. Said compositions are applied in effective amounts as any other plant food. The active ingredient may be admixed with other solids and applied as a conventional solid fertilizer, or it may be put into aqueous solution and applied either separately or with other liquid plant foods with conventional applicators in the form of, e.g., sprays.

The following examples serve to illustrate methods of application of the novel iron complexes of the present invention for the treatment of iron chlorosis in plants as well as the results obtained by such treatment.

EXAMPLE 3

Giant Besty Ross Chrysanthemum

In a greenhouse test chrysanthemums were grown in a quartz sand culture. A high pH nutrient solution was added to the growing medium. In the check treatment iron was withheld while in the other treatment the Example 1 iron complex (hereinafter CGA 20724) was added to the nutrient solution to supply iron. Visual observations of the growing plants were taken 9 and 17 days following treatment to measure the effect of the iron treatment.

|  | Chlorosis Ratings | |
| --- | --- | --- |
|  | 9 days | 17 days |
| Check | Very chlorotic | Severely chlorotic |
| CGA-20724 at .054 gms Fe/cubic foot of growing medium | Green | Very green |

CGA-20724 was very effective in supplying iron to the chrysanthemums. The check plants were chlorotic and grew very poorly while the treated plants were green and grew normally.

EXAMPLE 4

Soybeans were grown under controlled greenhouse conditions in pots in a high pH soil. The soil pH was 8.5. CGA-20724 was added to the soil and lightly incorporated into the surface at the rate of 2 ppm Fe. Leaf yields (mg/plant) and soil Fe (ppm) was measured after the soybeans were grown to indicate the effect of the treatments.

|  | Leaf Yield mg/plant | ppm Fe of soil |
| --- | --- | --- |
| Check | 170 | 29 |
| CGA-20724 at 2 ppm Fe | 541 | 51 |

The check plants were small and showed iron chlorosis of the leaves while the treated plants were green and healthy.

EXAMPLE 5

Soybeans

Soybeans were grown in pots in the greenhouse in a high pH iron deficient soil. CGA-20724 was added to the soil and lightly incorporated into the surface. Leaf yields and plant analysis of the leaves for Fe content were taken to determine the effect of the treatments.

|  | Leaf Dry weight mg/plant | Fa content of leaves (ppm) | Leaf Color |
| --- | --- | --- | --- |
| Check | 220 | 20 | Yellow |
| CGA-20724 at 1.5 lbs. Fe/A | 503 | 30 | Green |

Check plots had poor growth and remained yellow showing severe iron chlorosis while treated plants grew vigorously and remained green and healthy.

EXAMPLE 6

Hardee Soybeans

Soybeans were grown in one-gallon plastic tubs in a soil which had a pH of 8.0. CGA-20724 was added to the pots and lightly incorporated into the soil surface. Four replications were used in the test. After the plants were grown they were harvested and green weight yields taken to indicate treatment effect. Also leaf Fe content was determined by plant analysis to show iron uptake.

|  | Greenweight (gms) of Soybean Plants | Leaf Iron ppm Fe |
|---|---|---|
| Check | 63.9 | 69 |
| CGA-20724 at 0.6 lbs. Fe/A | 81 | 80 |

Plants treated with CGA-20724 produced higher yields and had higher leaf Fe content than untreated plants.

EXAMPLE 7

Bragg Soybeans

CGA-20724 was applied in a single band injected into the soil to the side and below the soybean seeds. The soil in which the test was run had a high pH.

The soybeans were grown for 60 days and then 5-foot plots were harvested and weighed. Green weights indicated response to treatments. Three replications were included in the test.

|  | Green Weight of Soybean Plants |
|---|---|
| Check | 32.7 ounces |
| CGA-20724 at 0.15 lbs. Fe/A | 46.0 ounces |

The CGA-20724 treatment increased the size and weight of the soybean plants.

EXAMPLE 8

Anoka Variety Soybeans

In a pot test with 5 gal. plastic tubs containing high pH iron deficient soil, 4 replications, grown outdoors, CGA-20724 iron chelate was added to the soil and mixed in the surface layer. Beans were planted, evaluated for greening response and shoot weights were taken at harvest.

| Foliar Greening Response | Early rating | Late rating |
|---|---|---|
| CGA-20724 at 0.9 lbs. Fe/A | 2.9 | 2.6 |
| Check | 1.5 | 1.6 |

The higher number over the check shows greening due to supply of Fe from CGA-20724. Therefore at both ratings, early and later in the growth cycle, the treated plants were much healthier than the checks.

| Shoot Weights at Harvest |  |
|---|---|
| CGA-20724 at 0.9 lbs. Fe/A | 5.8 gms |
| Check | 4.1 gms |

Plants treated with CGA-20724 had higher shoot weights than untreated plants.

EXAMPLE 9

Soybeans

In a greenhouse pot test with 4 replicates CGA-20724 iron chelate was added to a high pH iron deficient soil and mixed into the surface layer of the soil. Beans were planted. Greening responses, iron content of the leaves, and shoot weights were taken to determine response from the treatments.

| Application rate lbs.Fe/Acre | Fe, ppm of dry weight (leaves) | Shoot yield mg dry wt/plant | Greening |
|---|---|---|---|
| 0(check) | 33 | 261 | Yellow |
| 0.5 | 42 | 410 | Green and healthy |

Iron content of the leaves and shoot weights were statistically higher than the check. The check plants showed poor growth and were yellow while the treated plants were growing well, were green and healthy.

EXAMPLE 10

Navel Oranges

CGA 20724 was applied to the soil under the orange trees and lightly incorporated. One tree was used per treatment with 3 replications. The soil which the trees were growing in was high in pH and deficient in available iron. Treatments were applied in early May and visual ratings to determine treatment response were made periodically.

|  | Days After Treatment Application | | | |
|---|---|---|---|---|
|  | 0 | 30 | 120 | 240 |
| CGA-20724 18.75 gms Fe/tree | Slightly chlorotic | Green | Green | Green |
| Check | Slightly chlorotic | Slightly chlorotic | Moderately chlorotic | Very chlorotic |

Response of the tree as measured by greening effect on the leaves was excellent from the treatments. Untreated trees showed iron chlorosis on the leaves and die-back of terminal growth because of iron deficiency. Check trees produced a very poor crop of oranges while treated trees produced good fruit.

EXAMPLE 11

Vanguard Lettuce

CGA-20724 was applied to the soil in two bands on either side of the lettuce crop. Four replications were used in the test. Response of the treatments was measured by leaf analysis of the plants for iron to show if the iron was supplied to the crop by CGA-20724.

|  | Leaf analysis - ppm of Fe | | |
|---|---|---|---|
|  | Whole Plant early | Petioles early | Petioles late |
| Check | 231 | 310 | 84 |
| CGA-20724 at 0.9 lbs. Fe/A | 251 | 460 | 102 |

CGA-20724 as a soil application to lettuce did supply iron to the growing crop as shown by the leaf analysis data.

EXAMPLE 12

McCaslan 42 Pole Beans

CGA-20724 was applied as a soil drench treatment two weeks after seeding pole beans. Four replications were used in the test which was on a high pH iron deficient soil. The beans were grown to maturity and harvested. Yields were used to indicate treatment response.

| | Market Yield Cwt/A | Dollar Value/A at $6.00/bushel |
|---|---|---|
| Check | 45 | $900 |
| CGA-20724 at 0.6 lbs. Fe/A | 49 | $960 |

The CGA-20724 increased the yield of pole beans.

EXAMPLE 13

Peanuts

In a field test on peanuts growing on soil low in available iron with four replications, CGA-20724 was applied as sidedressing to the soil soon after the peanut crop emerged. Treatment response was measured by yield data.

| lbs/A Fe Applied | Yield of Peanuts lbs/A |
|---|---|
| 0(check) | 920 |
| 0.3 lbs. Fe/A | 1072 |

The yield of the treated peanuts were statistically higher than the check. Iron chlorosis of the leaves was evident during the growing season in the untreated plots.

EXAMPLE 14

Bartlett Pear Variety

In a field test on mature bearing pear trees growing on soil with low available iron content, one tree per plot, 4 replications, CGA-20724 iron chelate was applied to the soil under the trees in the spring and lightly incorporated into the soil. Leaves on the trees were showing iron deficiency symptoms. Visual ratings were taken 60 days later to assess the effect of the iron chelate treatment.

| Foliar Greening Response | | |
|---|---|---|
| Check | 2.5 | |
| CGA-20724 at 25 gms Fe/tree | 4.5 | |
| Rating scale | 1 = Severe chlorosis | |
| | 2 = Very Chlorotic | |
| | 3 = Slightly chlorotic | |
| | 4 = Pale green | |
| | 5 = Dark green | |

Treated trees were very green and healthy compared to the check. No signs of iron deficiency of the leaves were noted on the treated trees.

What is claimed is:

1. A composition of matter for the treatment of iron deficiencies in plants which comprises from about one-hundredth to about 50 percent by weight of at least one iron complex of ethylene-bis-($\alpha$-imino-2-hydroxyaryl acetic acid) as active ingredient of the formula

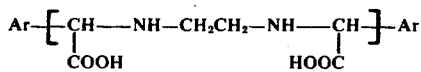

wherein Ar is selected from the group consisting of

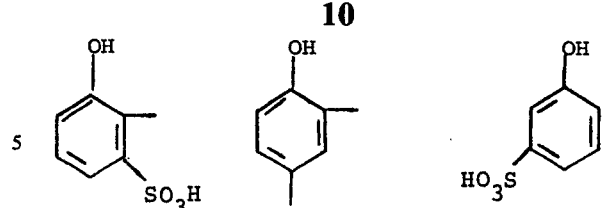

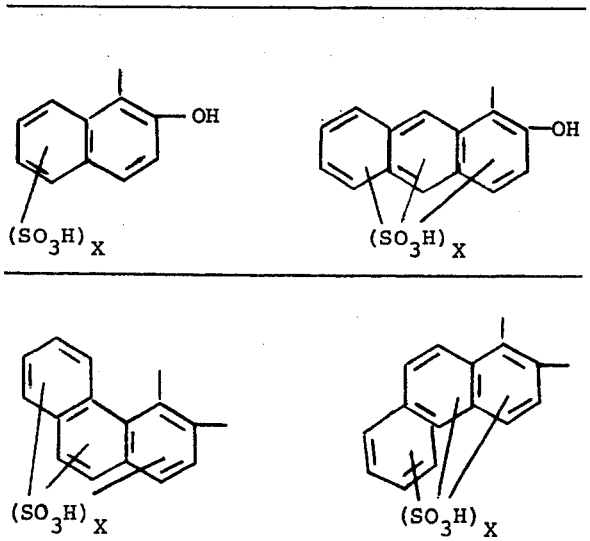

wherein X is 1 to 3
the molar ratio of ligand to iron being from about 1:1.1 to 1:3.0.

2. A composition as claimed in claim 1, wherein the ethylene-bis-($\alpha$-imino-2-hydroxyaryl acetic acid) has the formula

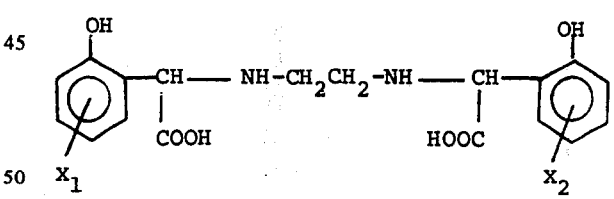

wherein $X_1$ and $X_2$ are each linked in the 3-, 4- or 5-position to the respective benzene nuclei and each represents —$SO_3H$ and wherein the molar ratio of ligand to iron is from about 1:1.0 to 1:2.0.

3. A composition as claimed in claim 2, wherein the ethylene-bis-($\alpha$-imino-2-hydroxyaryl acetic acid) is ethylene-bis-($\alpha$-imino-2-hydroxy-5-sulfophenyl acetic acid).

4. A composition as claimed in claim 2, wherein the ethylene-bis-($\alpha$-imino-2-hydroxyaryl acetic acid) is 1,1'-ethylene-bis-($\alpha$-imino-2-hydroxy-3,6-disulfo-2-naphthalene acetic acid).